(12) United States Patent
Li (10) Patent No.: US 7,042,322 B2
(45) Date of Patent: May 9, 2006

(54) HIGH-PERFORMANCE LIQUID MAGNETIZER

(76) Inventor: Chien-Hsing Li, No. 48, Singlong Rd., Jhongli City, Taoyuan County (TW)

( * ) Notice: Subject to any disclaimer, the term of this patent is extended or adjusted under 35 U.S.C. 154(b) by 0 days.

(21) Appl. No.: 10/815,821

(22) Filed: Apr. 2, 2004

(65) Prior Publication Data

US 2005/0219024 A1    Oct. 6, 2005

(51) Int. Cl.
*B01D 35/06* (2006.01)

(52) U.S. Cl. .............. 335/284; 335/302; 335/306; 210/222

(58) Field of Classification Search ........ 335/296–306, 335/284; 210/222–223; 123/538

See application file for complete search history.

(56) References Cited

U.S. PATENT DOCUMENTS

| | | | | |
|---|---|---|---|---|
| 4,904,381 A | * | 2/1990 | Urakami ..................... 210/223 |
| 5,673,674 A | * | 10/1997 | Monteiro Vieira .......... 123/538 |
| 5,882,514 A | * | 3/1999 | Fletcher ..................... 210/223 |
| 6,143,577 A | * | 11/2000 | Bisconte Sconte De Saint Julien ........... 436/526 |
| 6,247,459 B1 | * | 6/2001 | Liao ........................... 123/538 |

* cited by examiner

*Primary Examiner*—Ramon M. Barrera
(74) *Attorney, Agent, or Firm*—Troxell Law Office, PLLC (57) ABSTRACT

A high-performance liquid magnetizer including a powerful magnet and a fluid sink. A spiral fluid guide being disposed in the fluid sink. A first opening disposed at the center of the sink and a second opening on one side of the fluid guide. The liquid flowing through the first opening into the fluid guide towards the second opening. The spiral sink extending the magnetization time for the fluid while the revolving direction of the liquid help improve the magnetism field effects.

7 Claims, 11 Drawing Sheets

HIGH-PERFORMANCE LIQUID MAGNETIZER

BACKGROUND OF THE INVENTION (a) Field of the Invention

The present invention is related to a high-performance liquid magnetizer, and more particularly, to one that extends the magnetization time of liquid through a spiral fluid guide sink for improving magnetic filed effects generated by powerful magnet through the revolving direction of the liquid, and allowing applying of positive and negative magnetism filed effects in various natures of liquid.

(b) Description of the Prior Art

With the upgraded living standard and advanced development of medical technologies, everyone demands comparatively higher on his health care requirements. Therefore, publications of ways for health maintenance have been mush rooming, and among them, active water by magnetization is highly recommended. The process of magnetization involves use of powerful energy from magnetism filed to fission the molecular groups of water in the liquid to promote the liquid to create minute particles rendering the smaller water moles with increased activity. The liquid so magnetized containing smaller magnetic molecular groups is referred as the "active water of magnetization", which features high permeability, high dissolution power, lower attachment and excellent function to break up the interface in maintaining consistent water quality from being deterioration.

Whereas the magnetism filed effects vary depending on the positive or the negative magnetism filed is applied, the activities, thus the functions of the liquid differ depending on the type of magnetism field applied through. Wherein, the magnetization with positive magnetism brings the liquid to carry positive electrons to create activation and acidification and cause the electrons to revolve clockwise for them to be applied in all fuels containing hydrocarbon chemical compounds. Either the gas or liquid, once activated by passing through the positive magnetism filed to provide more complete combustion of the fuel, the purpose of fuel saving is achieved. On the contrary, the effects of negative magnetism filed will cause the liquid to carry negative electricity to produce reduction and alkalization and cause the electrons to revolve counter-clockwise, which is beneficial in the use of the water for health care. The potable water when subject to magnetization through negative magnetism filed will become the active water of magnetization of alkali nature to allow human body maintaining alkali, and to induce reduction, i.e., anti-oxidization to eliminate residue free radicals in human body for prevention of the development of carcinoma.

SUMMARY OF THE INVENTION

The primary purpose of the present invention is to provide a high-performance liquid magnetizer essentially comprised of powerful magnet and fluid sink. Wherein, a spiral fluid guide is disposed in the fluid sink with a spiral partitioning board; a first opening is disposed at the center of the fluid guide, and a second opening formed on one side of the fluid guide. Accordingly, when the liquid flows through the first opening into the fluid guide towards the second opening, the sink in spiral form will extend the magnetization time for the fluid while the revolving direction of the liquid help improve the magnetism field effects created by the power magnet to further enhance the magnetization results.

DETAILED DESCRIPTION OF THE PREFERRED EMBODIMENTS

Figure 1:
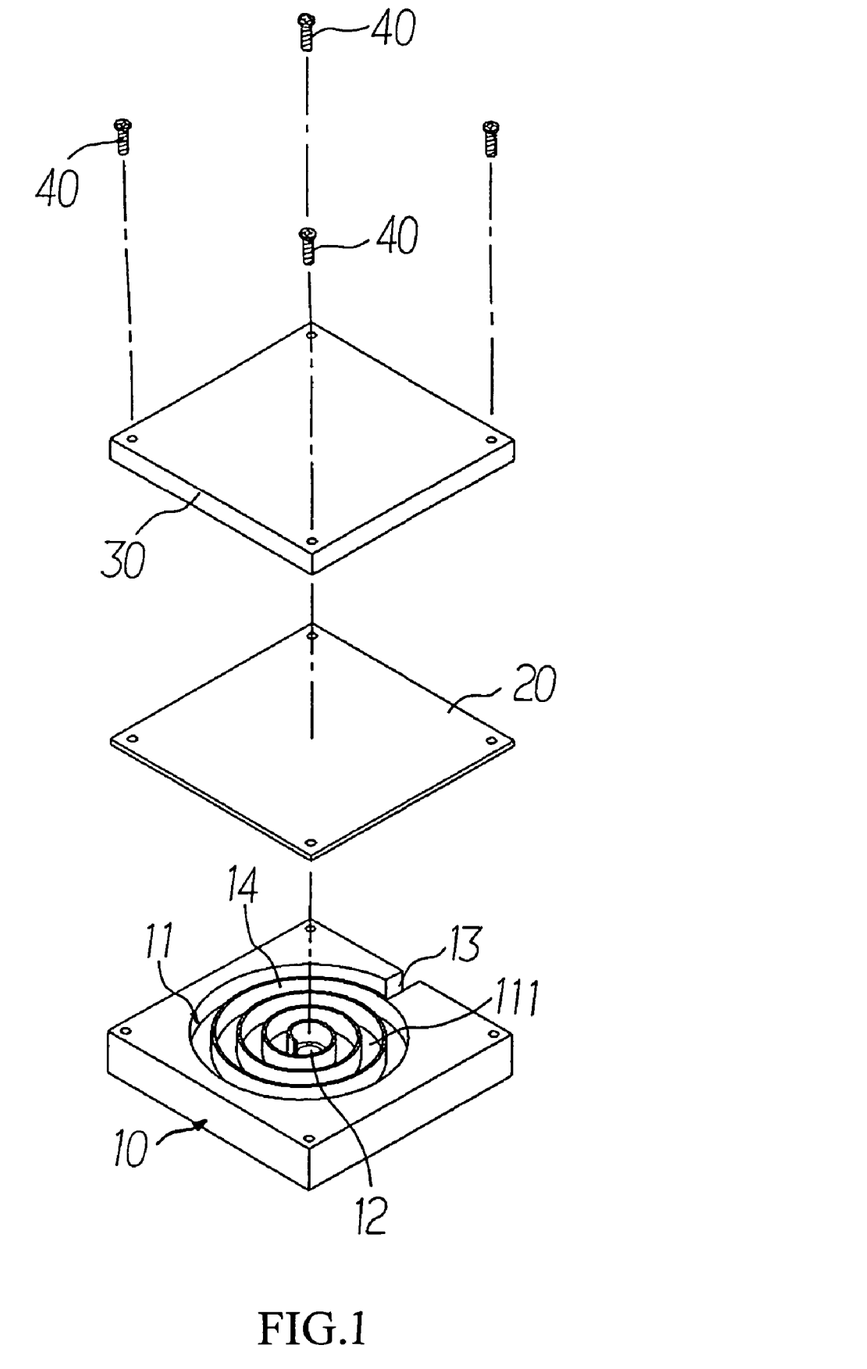
FIG. 1 is an exploded view of the structure of the present invention.

Referring to FIG. 1, the structure of a liquid magnetizer (A) of the present invention is comprised of a sink (10), a pad (20), and a powerful magnet (30). The pad (20) is made of silicon gel or rubber, and the power magnet (30) (in this preferred embodiment) relates to a large plate shape magnet.

Figure 2:
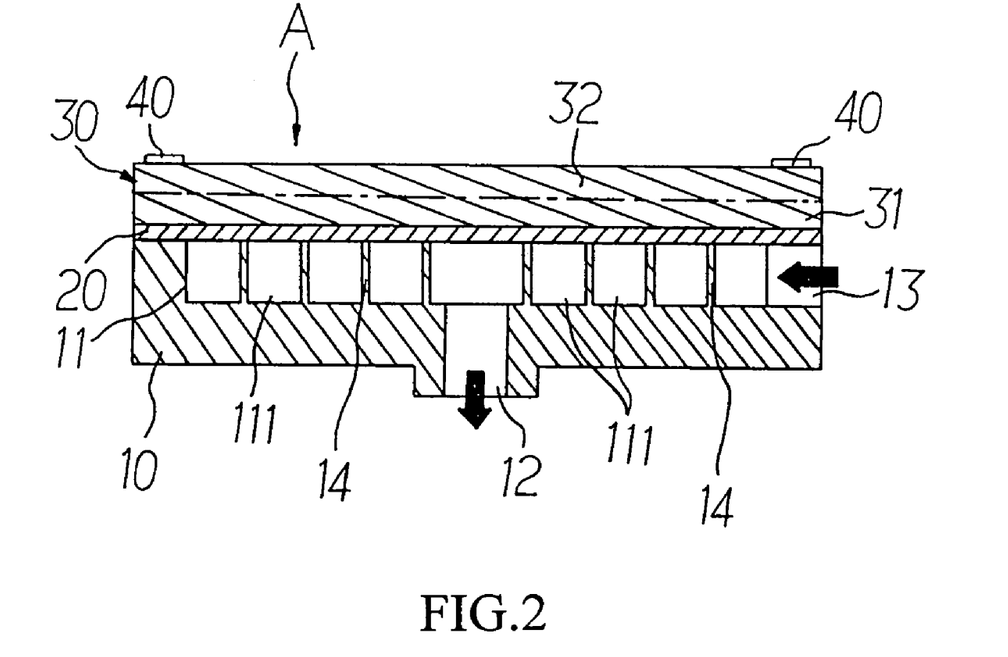
FIG. 2 is a side view of the present invention.

Also referring to FIG. 2, a guide (11) provided in the sink (10) contains a spiral guide sink (111) segregated by means of a spiral partitioning board (14). A first opening (12) is disposed at the center of the guide sink (111), a second opening (13) is formed on one side of the sink (10), and the pad (20) is provided over the sink (10) and is topped by the power magnet (30). The powerful magnet (30) has its N-pole (31) flushed against the pad (20) and is fixed in its four corners each with a screw (40) penetrating further the pad (20) and the sink (10).

Figure 3:
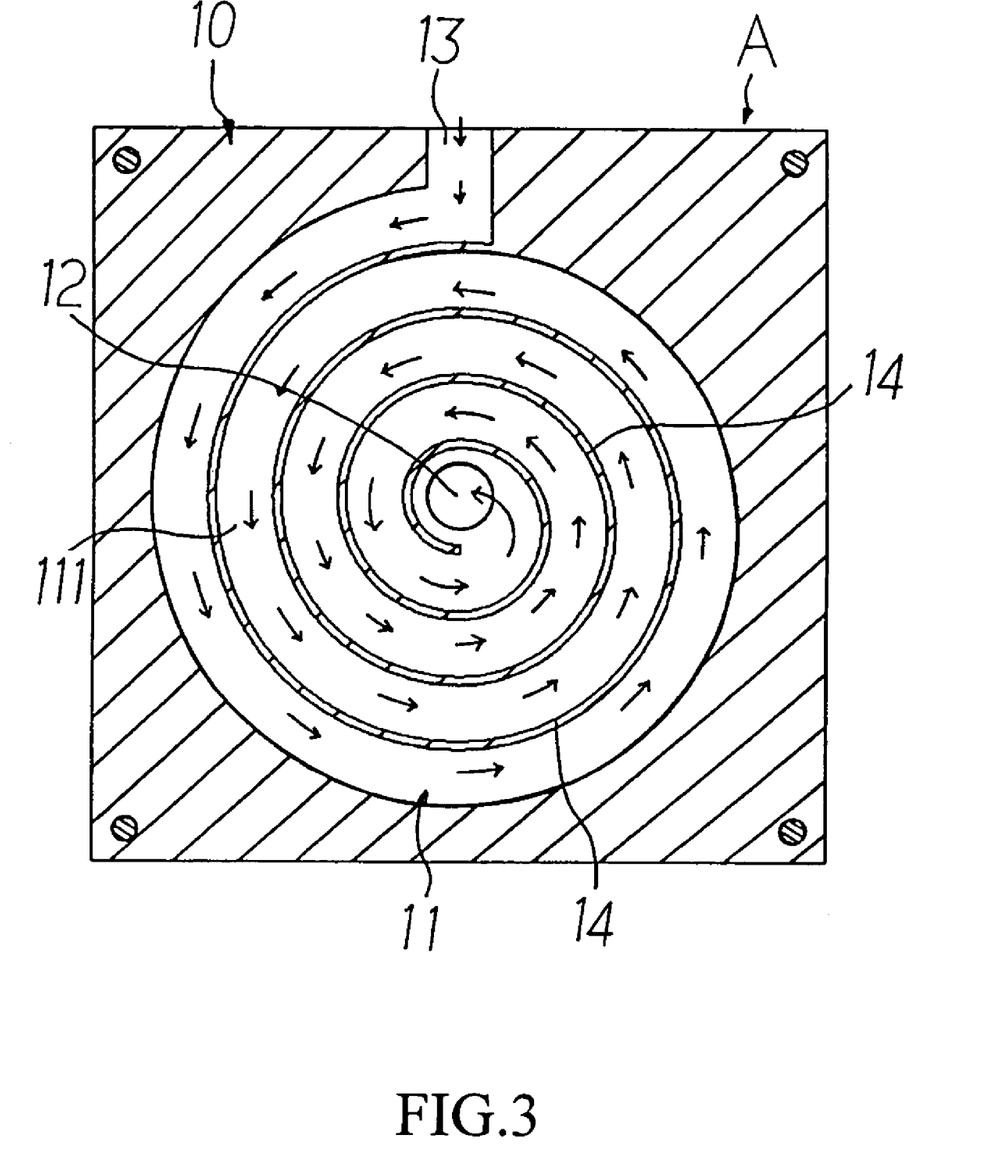
FIG. 3 is a schematic view showing the revolving of the liquid in the present invention.

When the liquid flows through the second opening (13) into the guide sink (111) towards the first opening (12) as illustrating in FIG. 3, the liquid revolves counter-clockwise. On one hand, the spiral configuration of the guide sink (111) extends the time for the liquid to be magnetized; and on the other hand, as the liquid revolves counter-clockwise, the effects of negative magnetism filed generated by the N-pole (31) of the powerful magnet (30) improves the magnetization results to allow the liquid magnetizer (A) to be used in the potable water for health care purpose. The potable water activated by the negative pole magnetization tends to be alkaline, thus to maintain alkali in human body, generate reduction for anti-oxidization purpose, and eliminate residual free radicals in human body to prevent the development of carcinoma.

Figure 4:
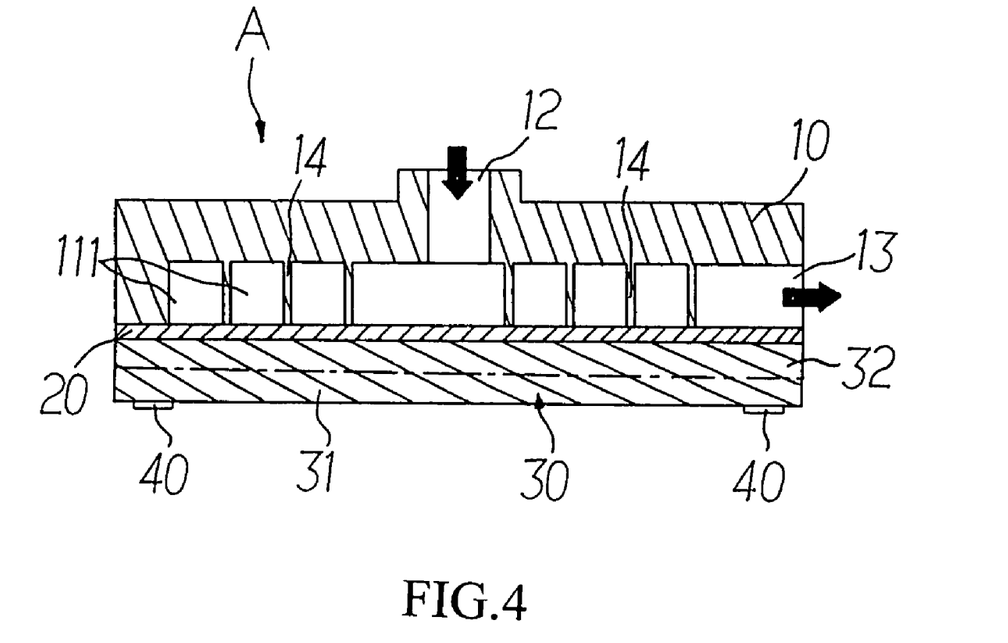
FIG. 4 is a side view of a structure of a first preferred embodiment of the present invention.
Figure 5:
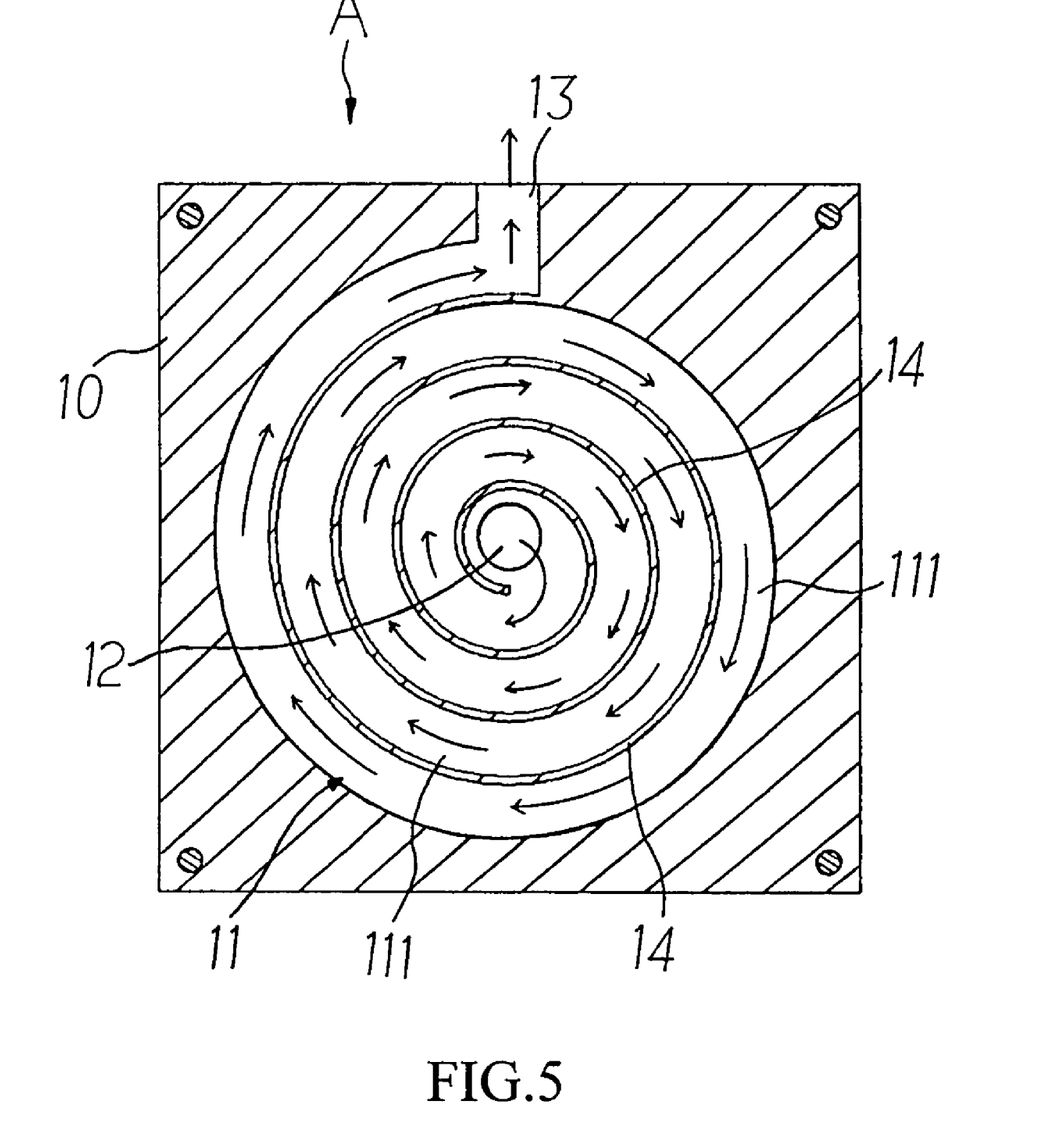
FIG. 5 is a schematic view showing the revolving of the liquid as illustrated in FIG. 4.
Figure 6:
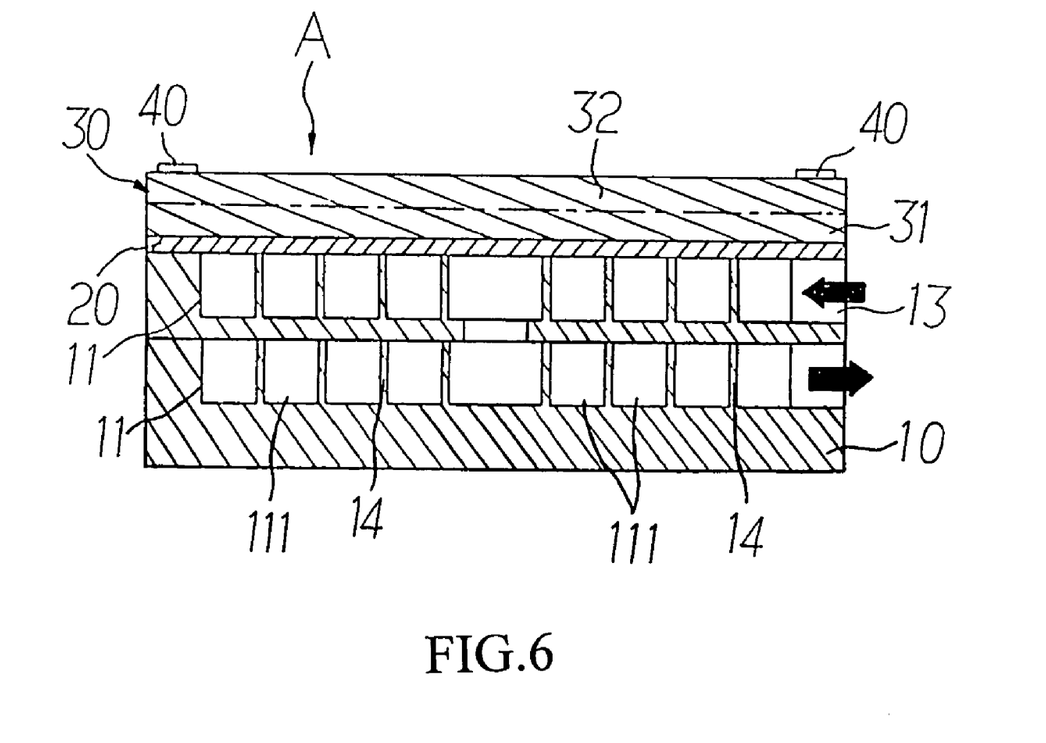
FIG. 6 is a side view of a structure of a second preferred embodiment of the present invention.

Referring to FIG. 4, another preferred embodiment of the present invention has the powerful magnet flushed against with its S-pole (32) to the pad (20). When the liquid flows into the guide sink (111) through the first opening (12) towards the second opening (13), the liquid revolves clockwise as illustrated in FIG. 5. On one hand, the spiral guide sink (111) permits longer time for the liquid to be magnetized; and on the other hand, as the liquid revolves clockwise, the positive magnetism filed effects generated by S-pole (32) of the powerful magnet (30) are intensified to improve magnetization results. The liquid magnetizer (A) can be applied in any type of fuel containing hydrocarbon chemical compounds. The fuel, either in the form of gas or liquid, once activated by passing through the positive magnetism filed contributes to complete combustion of the fuel to achieve the purpose of fuel saving. Alternatively, the liquid magnetizer (A) may be installed in a water pipe to remove scales; or multiple units of the sink (10) may be provided to further enhance the magnetization results as illustrated in FIG. 6.

Figure 7:
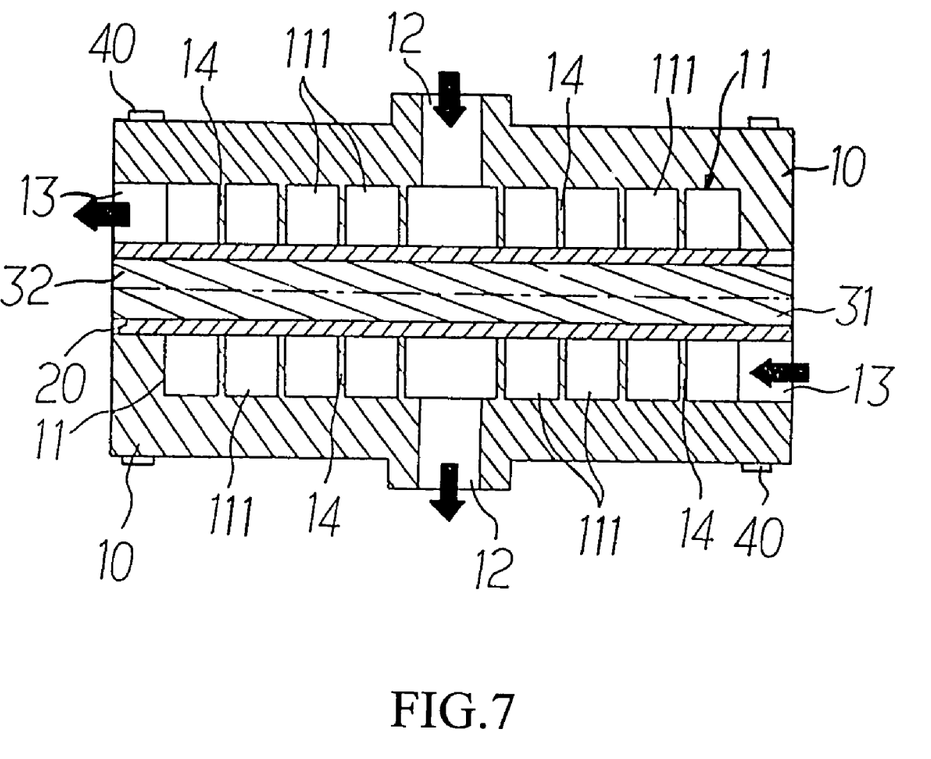
FIG. 7 is a side view of a structure of a third preferred embodiment of the present invention.

As illustrated in FIG. 7, another preferred embodiment yet of the present invention has two sinks (10) each attached with the pad (20) are respectively secured to the top and the bottom of the powerful magnet (30) with the liquid in the sink (10) contacting the S-pole (32) of the powerful magnet (30) to flow clockwise while that in another sink (10) contacting the N-pole (31) of the powerful magnet (30) to flow counter-clockwise to simultaneously provide north pole and south pole magnetization results for dual purposes of cleaning water and removing scales at the same time.

Figure 8:
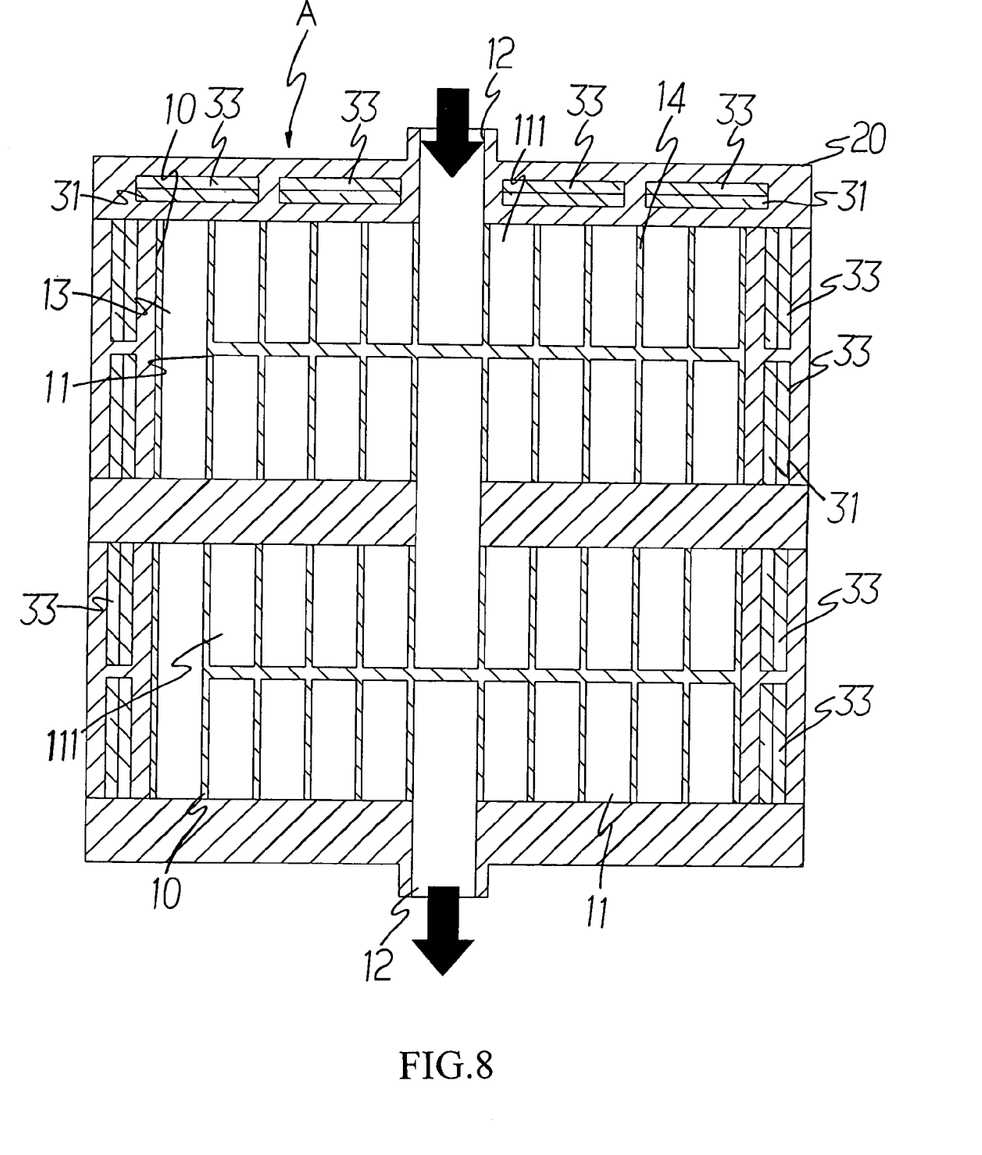
FIG. 8 is a side view of a structure of a fourth preferred embodiment of the present invention.
Figure 9:
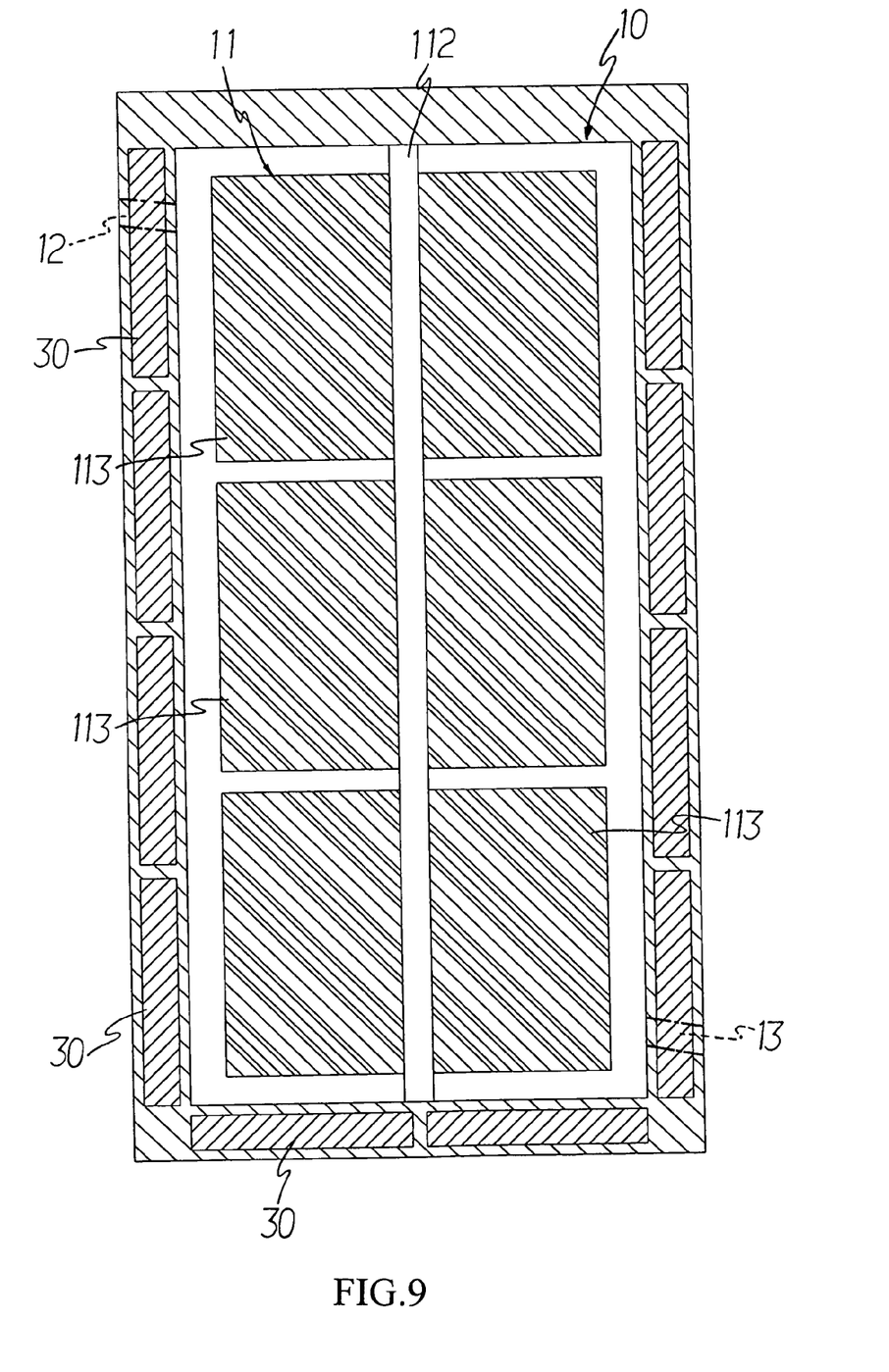
FIG. 9 is a side view of a structure of a fifth preferred embodiment of the present invention.

The powerful magnet (30) may be comprised of multiple smaller magnets (33) arranged on or by the sink (10) with the same poles facing the sink (10) as illustrated in FIG. 8. Wherein, all those smaller magnets (33) have their north poles (31) facing toward the sink (10) to provide negative magnetism field effects.

Figure 10:
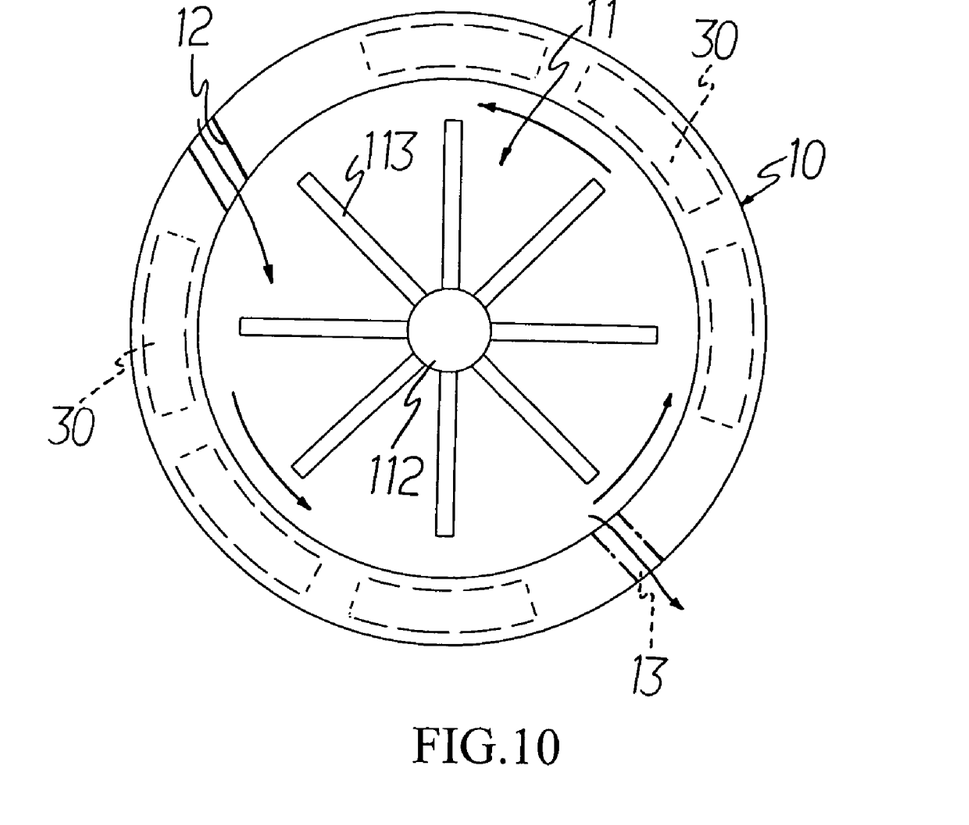
FIG. 10 is a side view of a structure of a sixth preferred embodiment of the present invention.
Figure 11:
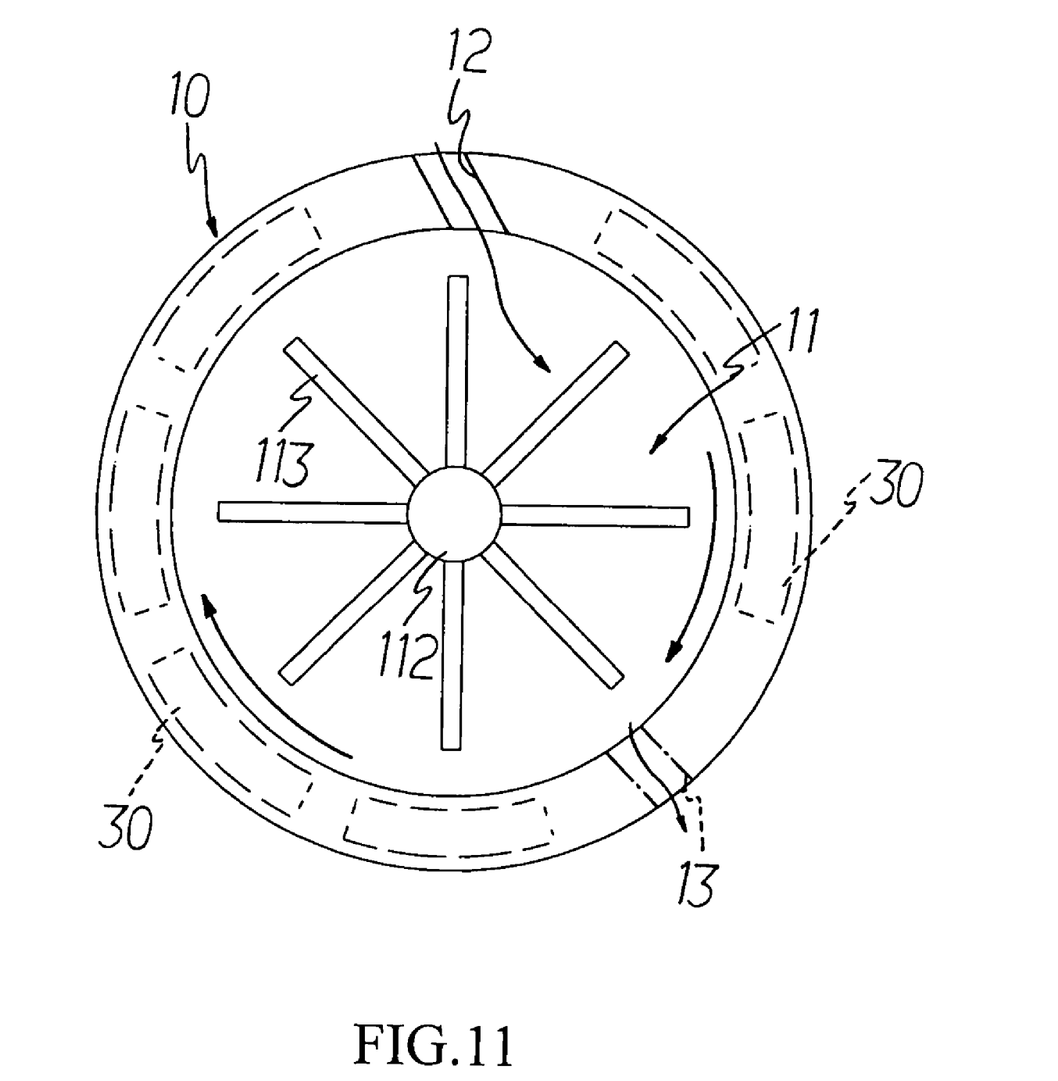
FIG. 11 is a side view of a structure of a seventh preferred embodiment of the present invention.

Furthermore, the guide (11) includes one segment (113) or multiple segments (113) to a same pivot (112) provided at the center of the center of the sink (10). Wherein, both of the first opening (12) and the second opening (13) are respectively provided above and below the sink (10) while multiple smaller magnets (33) are arranged either by or below the sink (10) with the same poles facing the sink (10). When the liquid flows through the first opening (12) into the sink (10), those segments (113) are driven to turn counter-clockwise as illustrated in FIG. 10 to revolve counter-clockwise towards the second opening (13) to be magnetized by negative magnetism. With the first opening (12) disposed at where as illustrated in FIG. 11, the liquid flows through the first opening (12) into the sink and drive those segments to turn clockwise for the liquid to be magnetized by the positive magnetism.

The high-performance liquid magnetizer of the present invention disclosed above by extending the time for the liquid to be magnetized, by improving the magnetization results from the magnetism filed effects created by the power magnet, and by providing magnetization for various natures of liquid from the positive and negative magnetism field effects is innovative, and a utility pattern application is duly filed accordingly; provided, however, that is should be noted that the preferred embodiments and the accompanying drawings are provided not to limit the present invention; therefore, any structure, device and/or characteristics that are similar to or identical with that of the present invention shall be deemed as falling within the objectives and claims of the present invention.

The invention claimed is:

1. A high-performance liquid magnetizer comprising: a sink provided with a first opening, a second opening, and a guide defining a given revolving direction for the liquid flowing between both openings; and a powerful magnet disposed on a top of the sink; the sink extending the time for the liquid being subject to magnetization, and further enhancing the magnetization results as the fluid revolves, wherein a pad is provided between the guide and the powerful magnet.

2. A high-performance liquid magnetizer as claimed in claim 1, wherein the pad relates to a silicon gel pad.

3. A high-performance liquid magnetizer as claimed in claim 1, wherein the pad relates to a rubber pad.

4. A high-performance liquid magnetizer comprising: a sink provided with a first opening, a second opening, and a guide defining a given revolving direction for the liquid flowing between both openings; and a powerful magnet disposed on a top of the sink; the sink extending the time for the liquid being subject to magnetization, and further enhancing the magnetization results as the fluid revolves, wherein the guide relates to a guide sink in spiral as segregated by a spiral partitioning board, wherein another guide sink segregated with a spiral guide plate in the direction opposite to the guide sink is provided below the guide sink.

5. A high-performance liquid magnetizer comprising: a sink provided with a first opening, a second opening, and a guide defining a given revolving direction for the liquid flowing between both openings; and a powerful magnet disposed on a top of the sink; the sink extending the time for the liquid being subject to magnetization, and further enhancing the magnetization results as the fluid revolves, wherein the guide relates to a guide sink in spiral as segregated by a spiral partitioning board, wherein two guides are respectively secured to the top and the bottom of the powerful magnet to simultaneously provide positive and negative magnetism field effects for cleaning water and removing scales in the water.

6. A high-performance liquid magnetizer comprising: a sink provided with a first opening, a second opening, and a guide defining a given revolving direction for the liquid flowing between both openings; and a powerful magnet disposed on a top of the sink; the sink extending the time for the liquid being subject to magnetization, and further enhancing the magnetization results as the fluid revolves, wherein the powerful magnet relates to a large plate magnet.

7. A high-performance liquid magnetizer comprising: a sink provided with a first opening, a second opening, and a guide defining a given revolving direction for the liquid flowing between both openings; and a powerful magnet disposed on a top of the sink; the sink extending the time for the liquid being subject to magnetization, and further enhancing the magnetization results as the fluid revolves, wherein the guide includes one of one segment and multiple segments connected to a pivot at the center of the sink; the first and the second openings being respectively provided at where above and below the sink; and the liquid flowing through the first opening into the sink to drive those segments turning clockwise and revolves towards the second opening.

* * * * *